(12) United States Patent
Moriyama et al.

(10) Patent No.: US 7,914,444 B2
(45) Date of Patent: Mar. 29, 2011

(54) ENDOSCOPE SYSTEM AND ENDOSCOPE

(75) Inventors: Hiroki Moriyama, Tokyo (JP); Seisuke Takase, Tokyo (JP); Masaaki Miyagi, Tokyo (JP)

(73) Assignee: Olympus Corporation, Tokyo (JP)

( * ) Notice: Subject to any disclaimer, the term of this patent is extended or adjusted under 35 U.S.C. 154(b) by 1323 days.

(21) Appl. No.: 11/452,812

(22) Filed: Jun. 14, 2006

(65) Prior Publication Data

US 2006/0235273 A1 Oct. 19, 2006

Related U.S. Application Data

(63) Continuation of application No. PCT/JP2004/018739, filed on Dec. 15, 2004.

(30) Foreign Application Priority Data

Dec. 15, 2003 (JP) ................... 2003-417076

(51) Int. Cl.
*A61B 1/018* (2006.01)
(52) U.S. Cl. ......... 600/113; 600/104; 600/129; 600/153
(58) Field of Classification Search ................. 600/113, 600/168, 130, 129, 104, 153, 173
See application file for complete search history.

(56) References Cited

U.S. PATENT DOCUMENTS

| | | | | |
|---|---|---|---|---|
| 3,924,608 A | * | 12/1975 | Mitsui | 600/107 |
| 4,436,087 A | * | 3/1984 | Ouchi | 600/106 |
| 4,588,294 A | | 5/1986 | Siegmund | |
| 6,059,719 A | * | 5/2000 | Yamamoto et al. | 600/127 |
| 6,063,095 A | * | 5/2000 | Wang et al. | 606/139 |
| 6,066,090 A | | 5/2000 | Yoon | |
| 6,117,071 A | * | 9/2000 | Ito et al. | 600/168 |
| 6,409,658 B1 | * | 6/2002 | Mitsumori | 600/167 |
| 6,991,602 B2 | * | 1/2006 | Nakazawa et al. | 600/101 |
| 7,156,863 B2 | * | 1/2007 | Sonnenschein et al. | 606/219 |
| 7,267,647 B2 | * | 9/2007 | Okada et al. | 600/166 |
| 7,662,089 B2 | * | 2/2010 | Okada et al. | 600/113 |
| 2001/0003142 A1 | * | 6/2001 | Koshikawa | 600/177 |
| 2005/0261674 A1 | * | 11/2005 | Nobis et al. | 606/45 |

FOREIGN PATENT DOCUMENTS

| | | |
|---|---|---|
| EP | 0 228 493 A1 | 7/1987 |
| JP | H04-102432 | 4/1992 |
| JP | 08-126606 | 5/1996 |
| JP | 2002-58635 | 2/2002 |
| JP | 2003-164412 | 6/2003 |
| JP | 2003-305001 | 10/2003 |

* cited by examiner

*Primary Examiner* — John P Leubecker
(74) *Attorney, Agent, or Firm* — Scully, Scott, Murphy & Presser, P.C.

(57) ABSTRACT

An endoscope system includes a first endoscope that includes a first distal end portion, a first observation window provided at the first distal end portion, a first objective optical system optically coupled to the first observation window and having a first viewing angle, and a first treatment instrument channel opening positioned at a first distance away from the first observation window; and a second endoscope that includes a second distal end portion, a second observation window provided at the second distal end portion, a second objective optical system optically coupled to the second observation window and having a second viewing angle wider than the first viewing angle, and a second treatment instrument channel opening positioned at a second distance longer than the first distance.

5 Claims, 5 Drawing Sheets

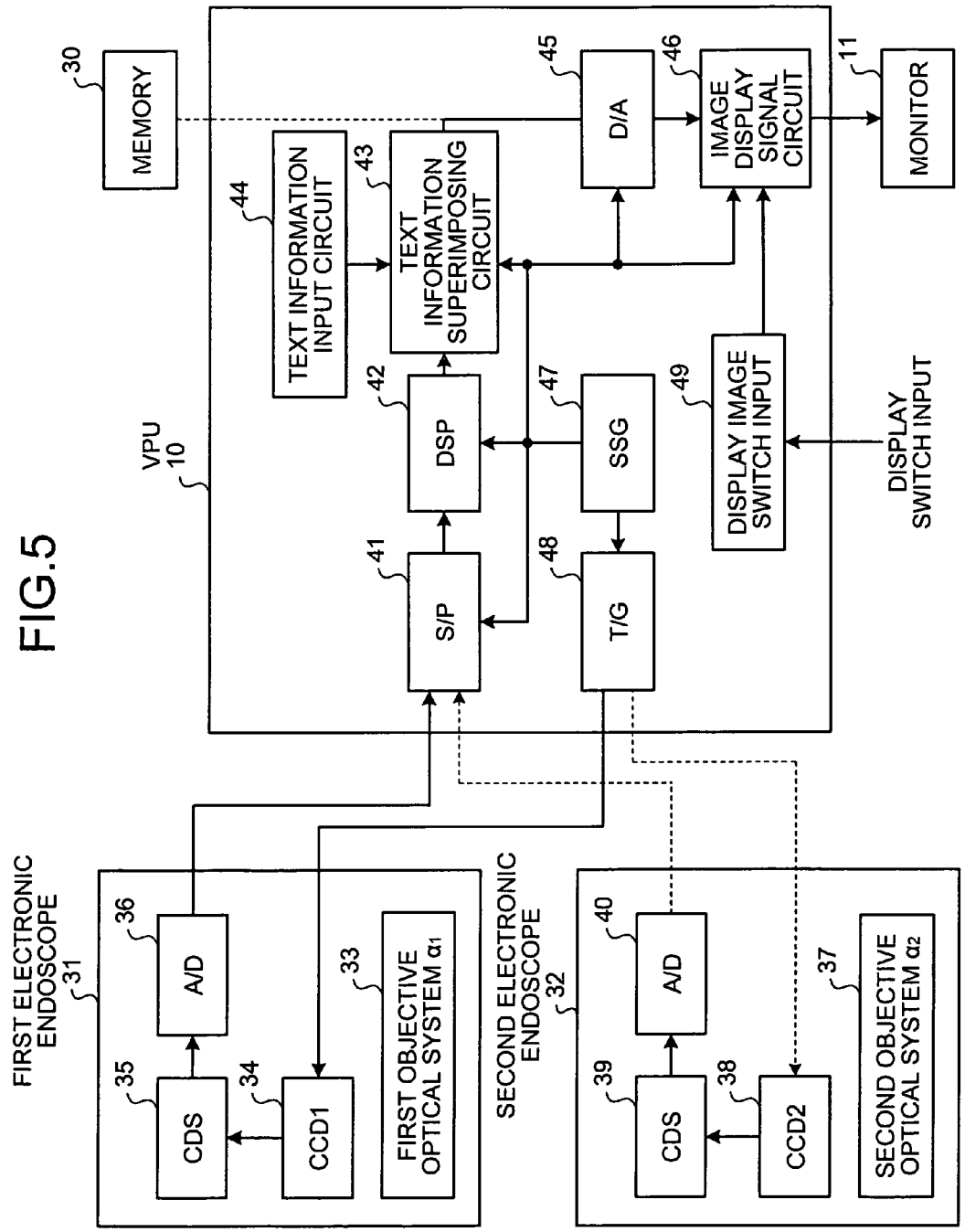

ENDOSCOPE SYSTEM AND ENDOSCOPE

CROSS-REFERENCE TO RELATED APPLICATIONS

This application is a continuation of PCT international application Ser. No. PCT/JP2004/018739 filed Dec. 15, 2004 which designates the United States, incorporated herein by reference, and which claims the benefit of priority from Japanese Patent Applications No. 2003-417076, filed Dec. 15, 2003, incorporated herein by reference.

BACKGROUND OF THE INVENTION

1. Field of the Invention

The present invention relates to an endoscope system including an endoscope having an objective optical system with a different viewing angle in an observation window at a distal end of an insertion unit, in which an installation position of a treatment instrument channel opening varies according to the viewing angle of the objective optical system.

2. Description of the Related Art

In recent years in a medical field, the endoscope device has been utilized to observe and operate organs within a body cavity by employing the endoscope which has at least a long insertion unit having the observation window, an illumination window, and the treatment instrument channel opening at its end part and an operating unit positioned at an proximal end of the insertion unit. Also, this endoscope device has been utilized in observing the inside of pipes in industrial fields.

The insertion unit of this endoscope device is comprised of a distal end portion in which the observation window, the illumination window, and the treatment instrument channel opening are provided, a bendable part adjacent to the proximal end of the distal end portion, and a flexible soft tube unit connected to the proximal end of the bendable part and a distal end of the operating unit. Also, an image guide, a light guide, and a treatment instrument channel are provided in the insertion unit. An end of the image guide is arranged in the objective optical system provided in the observation window. An end of the light guide is arranged in the illumination optical system provided in the illumination window. An end of the treatment instrument channel is communicated to the treatment instrument channel opening.

The operating unit of the endoscope device, has a bending operation knob, an eye piece, a treatment instrument insertion hole, and a universal cable. The bending operation knob enables its bendable part to be controlled as pulling a bending wire extended between the bending operation knob and the bendable part of the insertion unit. The eye piece enables an operator to view the observed region image as an ocular optical system is arranged at the proximal end of the image guide. The treatment instrument insertion hole communicates with the proximal end of the treatment instrument channel for a treatment instrument to be inserted therein. The universal cable has the built-in light guide to be connected to a light source.

Also, there is another endoscope in which a solid image element is provided at an image formation position of the objective optical system of an observation window and a signal cable sending and receiving a generated image signal as driving the solid image element is provided instead of the image guide.

Regarding the endoscope device of this type, the bendable part of the insertion unit is operated to be bent according to an internal shape of a tube to be inserted therein, the reflected light is introduced from the observed region illuminated with illumination light emitted from the illumination window of the distal end portion, and the operator observes the observed region image displayed on the eye piece of the operating unit as being transmitted by the image guide.

The viewing angle of the objective optical system of the observation window provided at the distal end portion of the insertion unit depends on observed region, and for example the objective optical system with a wide viewing angle is used to facilitate the observation of a lesioned part such as a back side of large intestine bag which is difficult to be observed. Also, a wide angle endoscope device, enabling to achieve a wide range observed region image, is proposed for example in Japanese Patent Application Laid-open No. H04-102432 Publication, wherein when the bending angle of the bendable part is limited according to the shape and size of the observed region, for example, the viewing angle of the objective optical system of the endoscope used to observe the observed region, which has a wide space and may have a large bending angle of the bendable part thereof, does not need to be widened as much, while the viewing angle of the objective optical system of the endoscope used to observe the observed region, which has a relatively narrow space and may have a small bending angle of the bendable part, is set wide.

Conventionally, the wide angle endoscope device with the wide angle objective optical system arranged in the observation window has been used so as to facilitate the observation of a lesioned part which is difficult to be observed, for example, the back side of the complex shape in the tube hole to be observed, such as a back side of large intestine bag.

On the other hand, while observing the position subject to be observed (observed region) by the endoscope device, the treatment instrument is projected from the treatment instrument channel opening toward the observed region to perform various operations such as organism system incision sampling. In the process of performing various organism system operations by this treatment instrument, the operator recognizes a physical relationship between the observed region and the treatment instrument from the position of the treatment instrument displayed by the observation figure obtained from the observation window of the distal end portion of the insertion unit to be observed at the eye piece or the observation image displayed on the monitor (hereinafter both are referred to as an observation image) and operates the treatment instrument.

In the case that the physical relationship between the actual observed region and the treatment instrument are the same, the physical relationship between the observed region and the treatment instrument in the observing image for the endoscope device, which has the objective optical system of a predetermined angle (e.g., 120 to 150 degrees) at the observation window of the distal end portion of the insertion unit and has a predetermined viewing angle, is mutually different from the physical relationship between the observed region and the treatment instrument in the observing image for the endoscope, which has the objective optical system of wider viewing angle (e.g., 151 degrees or more) at the operation window of the distal end part of the insertion unit than the viewing angle of the endoscope having the predetermined viewing angle (hereinafter referred to as a wide angle endoscope device).

That is, for example, if distances, i.e., the physical distances between the observation window and the treatment instrument at the distal end part of the insertion unit with respect to the endoscope device having the predetermined viewing angle and the wide angle endoscope device, are the same, the extent of projection of the treatment instrument projecting from the respective treatment instrument channel opening to reach the viewing angle of the objective optical system of the observation window with respect to the wide angle endoscope device is smaller than the extent of the projection with respect to the endoscope device having the predetermined viewing angle. That is, the wide angle endoscope device, because of the wide angle objective optical system of the observation window, reaches the viewing angle of the wide angle objective optical system while the amount of projection of the treatment instrument projecting from the treatment instrument channel is being small.

Therefore, when the operator operates the treatment instrument with the observation image of the wide angle endoscope, the treatment instrument appears in the observation image at the position where the treatment instrument slightly projects from the treatment instrument channel opening. As such, the operator may misunderstand that the treatment instrument projects to the same position for the endoscope with the predetermined viewing angle. Accordingly, there is a problem that the operator feels uncomfortable because of the difference in the physical relationship of the treatment instrument between the endoscope device with the predetermined viewing angle and the wide angle endoscope device.

Furthermore, generally, a fixed focus optical system is used in the objective optical system provided in the observation window of the endoscope. Therefore, especially, regarding the wide angle objective optical system, surrounding of the viewing angle comparing to the central part of the viewing angle slightly becomes out of focus. Accordingly, the treatment instrument immediately after being projected in the viewing angle of the wide angle objective optical system of the wide angle endoscope device temporary becomes unclear which possibly gives uncomfortable feeling to the operator.

SUMMARY OF THE INVENTION

An endoscope system according to one aspect of the present invention includes a first endoscope that includes a first distal end portion, a first observation window provided at the first distal end portion, a first objective optical system optically coupled to the first observation window and having a first viewing angle, and a first treatment instrument channel opening positioned at a first distance away from the first observation window; and a second endoscope that includes a second distal end portion, a second observation window provided at the second distal end portion, a second objective optical system optically coupled to the second observation window and having a second viewing angle wider than the first viewing angle, and a second treatment instrument channel opening positioned at a second distance longer than the first distance.

An endoscope system according to another aspect of the present invention includes a first endoscope that includes a first distal end portion, a first observation window provided at the first distal end portion, a first objective optical system optically coupled to the first observation window and having a first viewing angle, and a first treatment instrument channel opening into which a first treatment instrument is inserted; and a second endoscope that includes a second distal end portion, a second observation window provided at the second distal end portion, a second objective optical system optically coupled to the second observation window and having a second viewing angle different from the first viewing angle, and a second treatment instrument channel opening into which a second treatment instrument is inserted. Under a condition where an amount of projection of the first treatment instrument from the first treatment instrument channel opening is substantially the same as an amount of projection of the second treatment instrument from the second treatment instrument channel opening, a first distance between the first treatment instrument channel opening and the first observation window and a second distance between the second treatment instrument channel opening and the second observation window are set so that the first treatment instrument is in the first viewing angle and the second treatment instrument is in the second viewing angle.

An endoscope used in a system according to still another aspect of the present invention includes a first distal end portion; a first objective optical system which has at least a first viewing angle and is provided in the first distal end portion; and a first treatment instrument channel opening into which a first treatment instrument is inserted and which is provided in the first distal end portion. A first distance between the first treatment instrument channel opening and the first objective optical system at the first distal end portion is longer than a second distance between a second treatment instrument channel opening provided in a second distal end portion and a second objective optical system having a second viewing angle narrower than the first viewing angle, the second distal end portion, the second objective optical system, and the second treatment instrument channel opening constituting another endoscope used in the system.

An endoscope according to still another aspect of the present invention includes a distal end portion; an objective optical system having at least a predetermined viewing angle and provided in the distal end portion; and a treatment instrument channel opening into which a treatment instrument is inserted and is disposed at a distance, determined based on the viewing angle, away from the objective optical system.

An endoscope according to still another aspect of the present invention includes a distal end portion; an objective optical system having at least a first viewing angle and provided in the distal end portion; and a solid imaging element having a number of pixels larger than that of another solid imaging element for an objective optical system having a second viewing angle narrower than the first viewing angle.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is a block diagram showing the structure of the endoscope.

DETAILED DESCRIPTION OF THE PREFERRED EMBODIMENTS

Figure 1A:
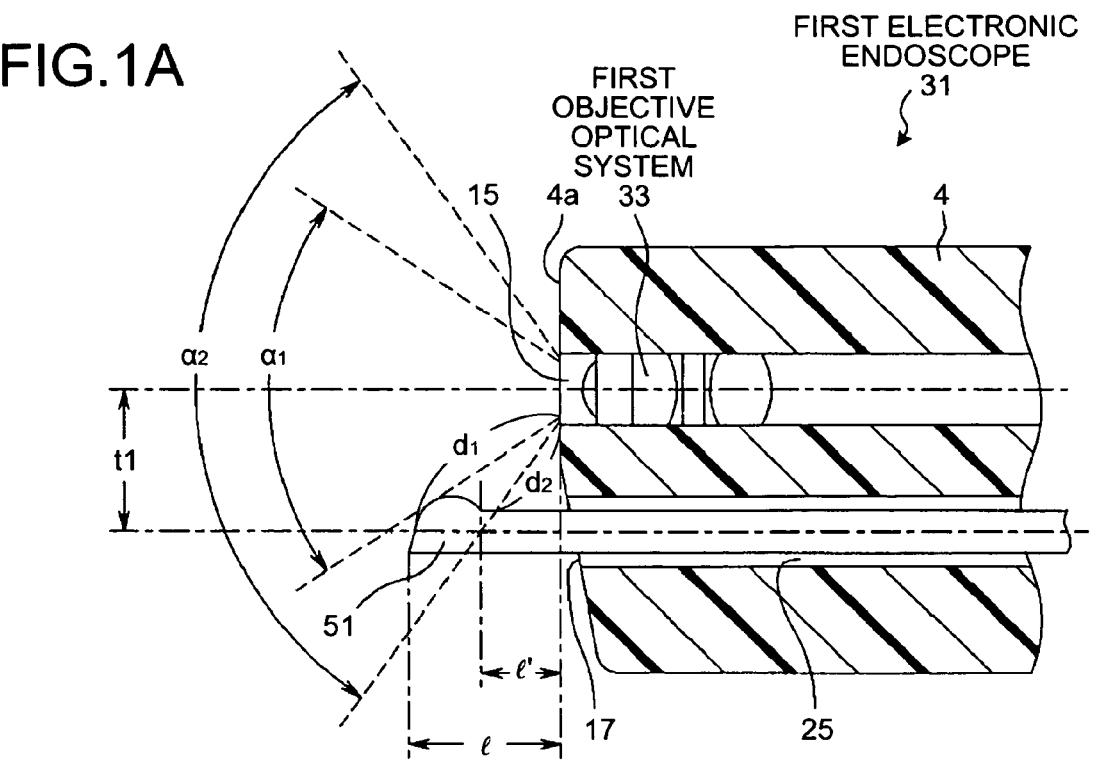
FIG. 1A is a cross-sectional view illustrating a distal end portion of one endoscope employed in an endoscope system according to the present invention.
Figure 1B:
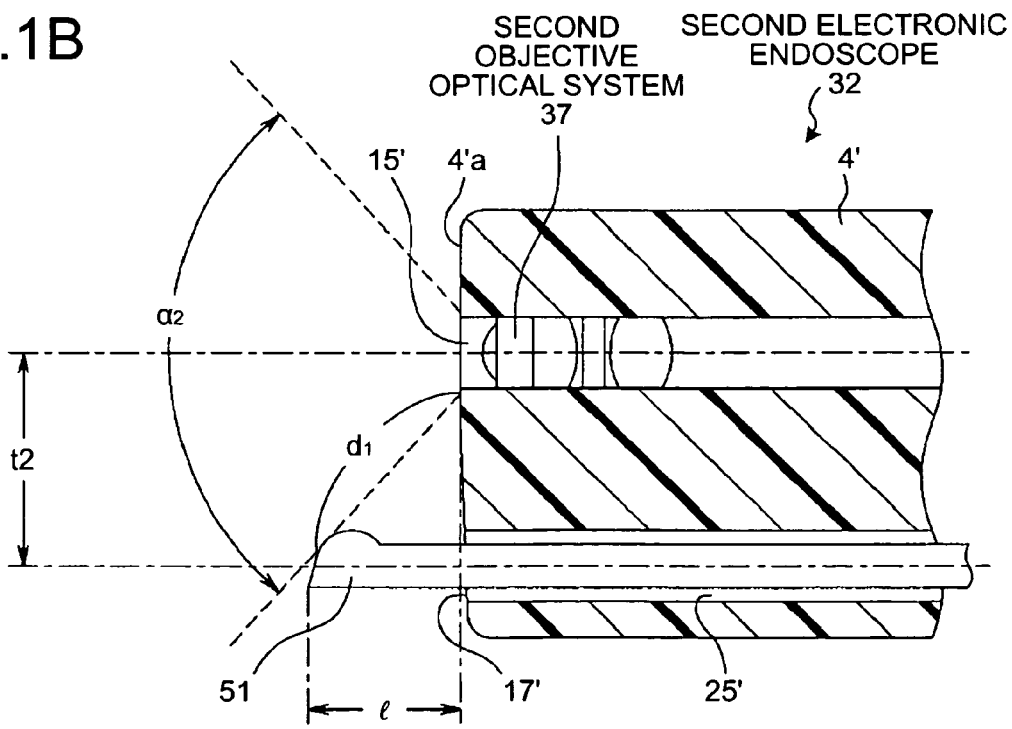
FIG. 1B is a cross-sectional view illustrating a distal end portion of another endoscope employed in the endoscope system.
Figure 2:
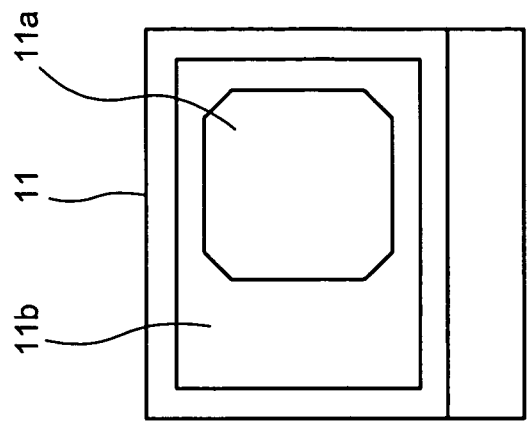
FIG. 2 is a block diagram showing general structure of the endoscope employed in the endoscope system.
Figure 2:
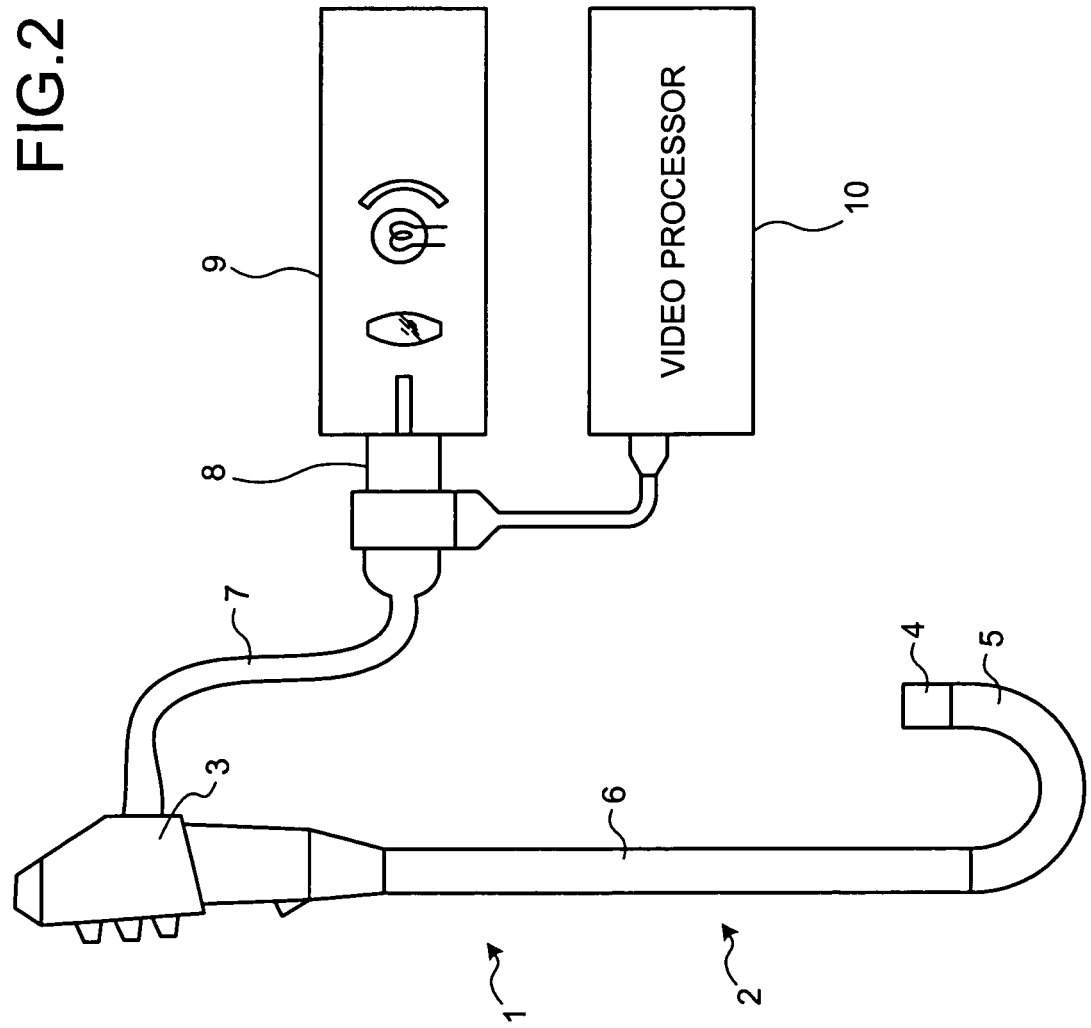
Figure 3:
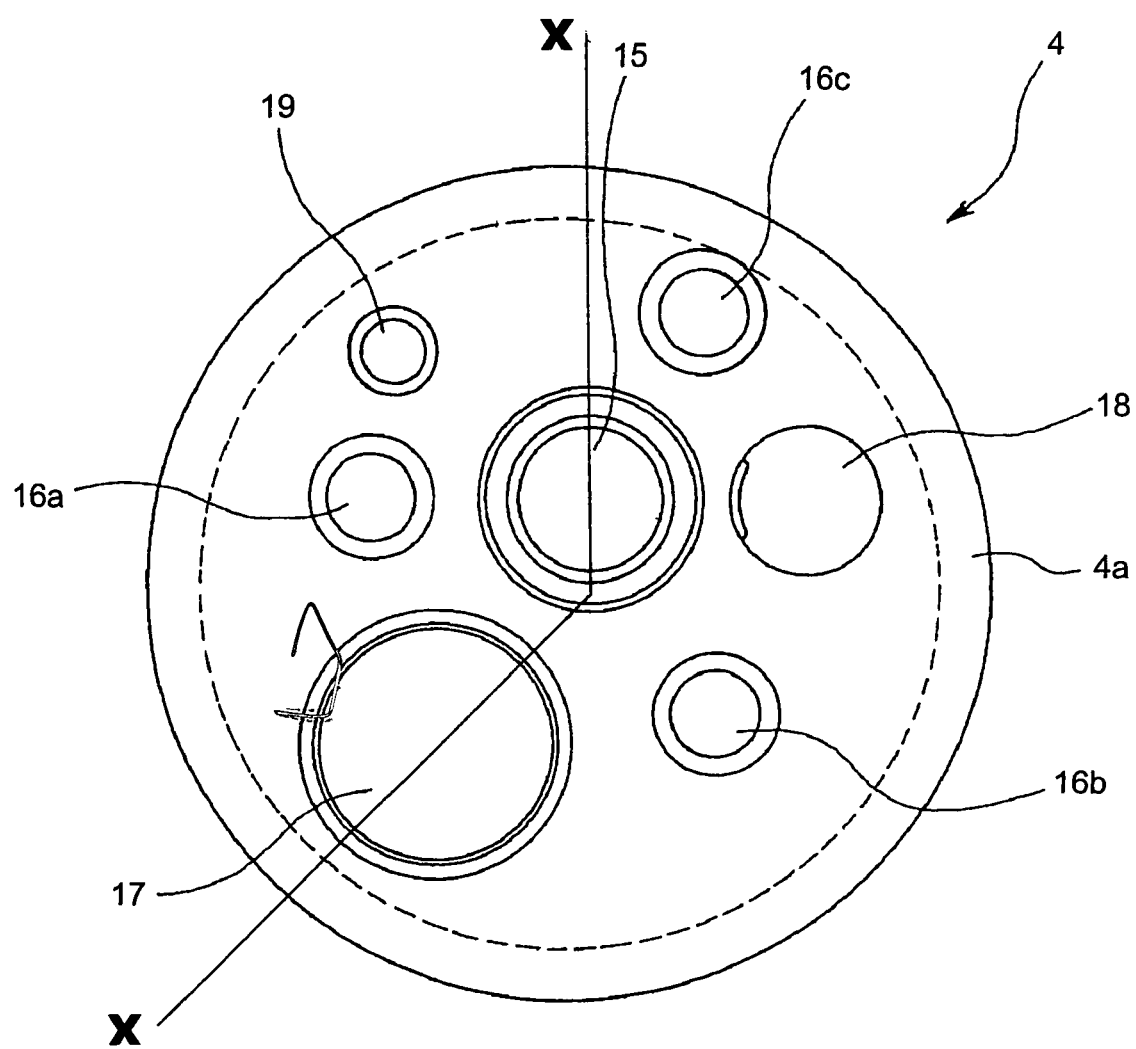
FIG. 3 is a front view illustrating the structure of the distal end portion provided in the insertion unit of the endoscope.
Figure 4:
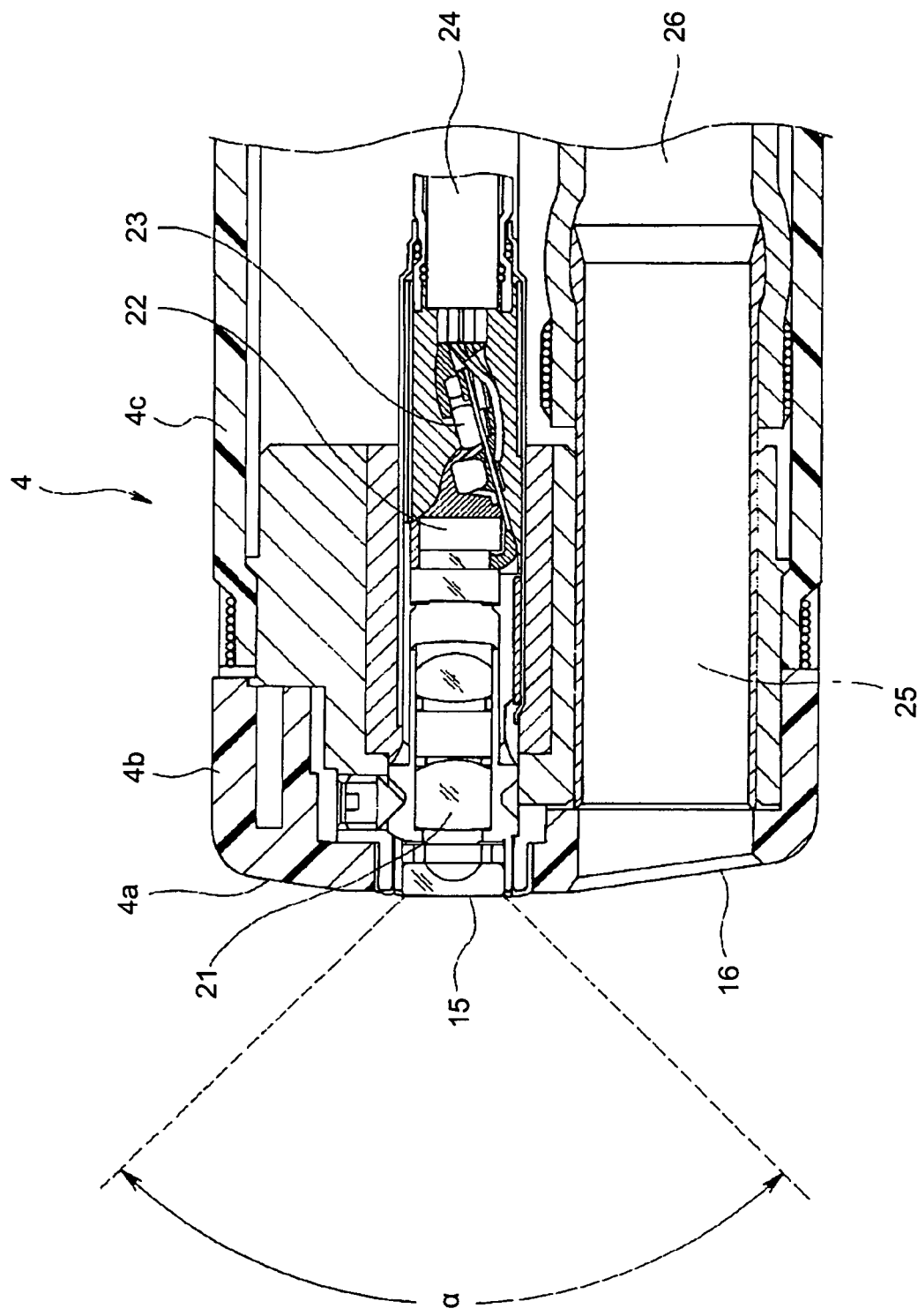
FIG. 4 is a cross-sectional view illustrating the structure of the distal end portion provided in the insertion unit of the endoscope.

Exemplary embodiments of an endoscope system according to the present invention will be explained with reference to FIGS. 1 to 5. FIGS. 1A and 1B are cross-sectional views illustrating the relationship between two endoscopes employed in the endoscope system according to the present invention; FIG. 2 is a block diagram showing general structure of the endoscope device employed in the endoscope system according to the present invention; FIG. 3 is a front view illustrating the structure of the distal end portion provided in the insertion unit of the endoscope employed in the endoscope system according to the present invention; FIG. 4 is a cross-sectional view illustrating the structure of the distal end portion provided in the insertion unit of the endoscope employed in the endoscope system according to the present invention; and FIG. 5 is a block diagram showing the structure of the endoscope device employed in the endoscope system according to the present invention.

To begin with, general structure of the endoscope device employed in the endoscope system according to the present invention will be explained with reference to FIG. 2. The endoscope device is comprised of an endoscope 1, a light source 9, a video processor 10, and a monitor 11. The endoscope 1 includes an insertion unit 2 composed of a distal end portion 4, a bendable part 5, and a flexible part 6, an operating unit 3 jointed to a proximal end of the insertion unit 2, a universal cable 7 extending out from the operating unit 3, and an endoscope connector 8 provided at the end of the universal cable 7.

The distal end portion 4 of the endoscope 1 provided with such as an illumination window, an observation window, a treatment instrument channel opening, and a water and air feeding opening, which are not shown in the figures. At the observation window of the distal end portion 4, the objective optical system to guide the reflecting light from the observed region therein is provided, and a solid imaging element is provided at an image formation position of the objective optical system. The bendable part 5 jointed to the distal end portion 4 has plural curved coma and is vertically and horizontally bent by a bending wire extended out from the bending operation knob as an example of a bending operation input unit provided at the operating unit 3. The flexible part 6 jointed to this bendable part 5 is made from a long flexible member.

A light guide, a signal cable, a treatment instrument channel, and a water and air feeding channel are provided at the distal end portion 4, the bendable part 5, and the flexible part 6. An end of the light guide is arranged at the illumination window of the distal end portion 4. The end of the signal cable is connected to the solid imaging element provided at the observation window. The end of the treatment instrument channel is arranged at the treatment instrument channel opening of the distal end portion 4. The end of the water and air feeding channel is arranged at the water and air feeding opening of the distal end portion 4.

The proximal end of the light guide is connected to the light source 9 from the operating unit 3 via the universal cable 7 and the endoscope connector 8. The proximal end of the signal cable is connected to the video processor 10 from the operating unit 3 via the universal cable 7 and the endoscope connector 8. The proximal end of the treatment instrument channel is connected to the treatment instrument insertion hole provided at the operating unit 3. The proximal end of the water and air feeding channel is connected to the sleeve of the water and air feeding channel provided at the operating unit 3 and feed water and air by a water and air feeding switch provided at the operating unit 3.

The light source 9 has an illumination lump and a light control circuit for the illumination lump and projects emitting light to the proximal end of the light guide of the endoscope connector 8. The video processor 10 drives a solid imaging element provided at the distal end portion 4 and receives an image signal of the observed region obtained by the solid imaging element therein to process a predetermined signal processing relative to the image signal, thereby generating the image signal. The monitor 11 displays the image of the observed region imaged by the solid imaging element (hereinafter referred to as the observation image) on the endoscope image display area 11a based on the image signal generated at the video processor 10. Furthermore, the monitor 11 displays, in addition to the observation image, information of, for example, name, age, and gender of the patient, and date of endoscope observation on a patient information display area 11b at the same time.

The structure of the distal end portion 4 of the insertion unit 2 in the endoscope device will be explained with reference to FIGS. 3 and 4. Here, FIG. 3 is a front view of the end surface of the distal end portion 4, viewed form the front thereof, and FIG. 4 is a cross-sectional view taken along cutting line X-X of FIG. 3 as cutting the distal end portion 4 in an axial direction.

At the end surface 4a of the distal end portion 4, as shown in FIG. 3, there are provided an observation window 15, plural illumination windows 16a, 16b, and 16c arranged at substantially equal intervals around the observation window 15, a treatment instrument channel opening 17, a water and air feeding nozzle 18 feeding water and air to the observation window 15, and a forward water feeding opening 19.

The distal end portion 4 includes an end cap 4b and a cylindrical cover 4c, and an internal structure, as shown in FIG. 4, is designed such that an objective optical system 21 including plural optical lenses with an viewing angle α is arranged at the observation window 15 provided on an end surface 4a of the end cap 4b. A solid imaging element 22 is arranged at the image formation position of the objective optical system 21. A circuit board 23, which has circuit functions to perform the drive control of the solid imaging element 22 and to receive the image signal generated by photoelectric conversion, is connected at a rear side of the solid imaging element 22. The signal cable 24 is connected to the circuit board 23, and the proximal end of the signal cable 24 is connected to the video processor 10.

The treatment instrument channel opening 17 provided at the end surface 4a of the end cap 4b communicates the treatment instrument channel 26 via a substantially cylindrical treatment instrument insertion cylinder 25. Also, the illumination lens, not shown in the figures, is provided at the illumination windows 16a to 16c provided at the end surface 4a of the distal end portion 4, and the end of the light guide is arranged at the illumination lens. Furthermore, the water and air feeding channel and the forward air feeding channel, not shown in the figures, communicate the water and air feeding nozzle 18 and the forward water feeding opening 19, respectively.

The endoscope system employing the endoscope 1 having the distal end portion 4 with the above-structure employed in the endoscope system 1 relating to the present invention will be explained with reference to FIG. 5. This endoscope system includes a first electronic endoscope 31 and a second electronic endoscope 32 equivalent to the endoscope 1, the video processor (hereinafter referred to as VPU) 10, and the monitor 11. Furthermore, the light source for generating illumination light to be projected to the observed region from the electronic endoscopes 31, 32 is not shown in the figures.

The first electronic endoscope 31 includes a first objective optical system 33 composed of plural lenses with general viewing angle (120 to 150 degrees) α1, a first solid imaging element (hereinafter referred to as a first CCD) 34 arranged at the image formation position of the first objective optical system 33 to image the observed region, a CDS circuit 35 performing a correlation double sampling processing of the image signal generated by the first CCD 34, and an analog-digital conversion circuit (hereinafter referred to as an A/D circuit) 36 converting analog image signal processed at the CDS circuit 35 to digital image signal.

The second electronic endoscope 32 includes a second objective optical system 37 composed of plural lenses with greater viewing angle (151 degrees or more) $\alpha 2$ ($\alpha 1 < \alpha 2$) than that of the first objective optical system 33 of the first electronic endoscope 31, a second solid imaging element (hereinafter referred to as a second CCD) 38 arranged at the image formation position of the second objective optical system 37 to image the observed region, a CDS circuit 39 performing a correlation double sampling processing of the image signal generated by the second CCD 38, and an analog-digital conversion circuit (hereinafter referred to as an A/D circuit) 40 converting analog image signal processed at the CDS circuit 39 to digital image signal.

The VPU 10 includes a separating process circuit (hereinafter referred to as S/P circuit) 41, a digital signal process circuit (hereinafter referred to as DSP circuit) 42, a text information duplex circuit 43, an alphabetic information input circuit 44, a digital-analog signal conversion circuit (hereinafter referred to as D/A circuit) 45, an image display signal circuit 46, a reference signal generating circuit (hereinafter referred to as SSG) 47, a timing signal generating circuit (hereinafter referred to as T/G circuit) 48, and a display image switch input circuit 49.

The S/P circuit 41 separates, for example, a luminance signal and a color signal for the digital image signal from the A/D circuit 36 of the first electronic endoscope 31 or the digital image signal from the A/D circuit 40 of second electronic endoscope 32. The DSP 42 performs a predetermined digital signal process with respect to the separated luminance signal and color signal at the S/P circuit 41 and at the same time performs correction such as white balance and γ correction, thereby generating the digital endoscope image signal.

The text information superimposing circuit 43 superimposes the text information indicating the information about the patient such as patient's name, age, gender, and date of endoscope observation on the digital endoscope image signal signal-processed in the DSP circuit 42. In the text information superimposing circuit 43, the superimposed text information signal, in the text information input circuit 44, is generated by the patient information input by the operator through a keyboard, not shown in the figures. In this text information superimposing circuit 43, the digital endoscope image signal, on which the text information is superimposed, is converted into the analog endoscope image signal in the D/A circuit 45 to be output to the image signal circuit 46. Furthermore, in the text information superimposing circuit 43, the digital endoscope image signal, on which the generated text information signal is superposed, is recorded in a memory 30 detachably provided on the VPU 10.

The image display signal circuit 46 converts and generates the image signal for displaying the observation image and the patient information on the monitor 11 based on the analog endoscope image signal supplied from the D/A circuit 45. This image display signal circuit 46 changes and sets, for example, the display position of the observation image and the patient information and size of the display image to be displayed on the monitor 11 by the control signal from the display image switch input circuit 49. For the display image switch input circuit 49, although it is not shown in the figures, it is possible to send commands for, e.g., the observation image, the display position of the patient information, and size of the display image that the operator displays on the monitor 11.

The SSG circuit 47 generates and outputs a reference signal which controls driving of the S/P circuit 41, the DSP circuit 42, the text information superimposing circuit 43, the D/A circuit 45, and the image display signal circuit 46. The T/G circuit 48 generates the timing signal of the drive control of the first and second CCDs 34, 38 for the first and second electronic endoscopes 31, 32, respectively from the reference signal from the SSG circuit 47.

In addition, the first electronic endoscope 31 and the second electronic endoscope 32 are connected to the VPU 10 using a connector as necessary or constantly connected, thereby enabling to switch the connection by a switch which is not shown in the figures.

Next, the structure of the distal end portion 4 of the insertion unit 2, in which the first and the second objective optical systems 33, 37 of the first and the second electronic endoscopes 31, 32 are arranged respectively, will be explained with reference to FIG. 1. Here, this FIG. 1 shows a model relationship between the first and the second objective optical system provided in the observation window 15 at the distal end portion 4 and the treatment instrument channel opening 17.

FIG. 1A shows the distal end portion 4 of the first electronic endoscope 31. The observation window 15, the treatment instrument channel opening 17, and the illumination windows 16a to 16c, the water and air feeding nozzle 18, and the forward water feeding opening 19, which are not shown in the figures, are provided at the distal end portion 4 of the first electronic endoscope 31. The first objective optical system 33 having the viewing angle $\alpha 1$ is arranged in the observation window 15 of the first electronic endoscope 31. A center axle of the observation window 15 of this distal end portion 4 and a center axle of the treatment instrument channel opening 17 on the end surface are arranged to have the physical relationship with an interval as appeared as t1 in the figure. Because of the physical relationship between the observation window 15 provided at the first objective optical system 33 of the viewing angle $\alpha 1$ and the treatment instrument channel opening 17 positioned with a distance t1 from the observation window 15, the treatment instrument 51 inserted and projected in the direction toward observed region from the treatment instrument channel opening 17 needs to be projected beyond an amount of projection l in the figure so as to project in a range of the viewing angle $\alpha$ of the first objective optical system 33. The treatment instrument 51 projecting in the viewing angle $\alpha 1$ can be observed from the observation window 15, and the physical relationship of the observed region and the treatment instrument 51 can be recognized.

Next, the observation windows 15 has the physical relationship with the treatment instrument channel opening 17 away therefrom to the distance of t1, and when the second objective optical system 37 with the viewing angle $\alpha 2$, which is wider than the viewing angle $\alpha 1$ of the first objective optical system 33 is installed in the observation window 15 of the distal end portion 4 to constitute the second electronic endoscope 32, the treatment instrument 51 projecting from the treatment instrument channel opening 17 proceeds in the range of viewing angle $\alpha 2$ with an amount of projection l' (l>l') in the figure much smaller than the amount of projection l.

As such, the treatment instrument 51 proceeds in the range of the wide viewing angle $\alpha 2$ of the second objective optical system 37 with slight amount of projection l'. The amount of projection l' of the treatment instrument 51 in this viewing angle α2 is not sufficient in view of the physical relationship with the observed region.

Then, as shown in FIG. 1B, at a distal end portion 4' of the second electronic endoscope 32, the second objective optical system 37 with the viewing angle α2 is arranged in an observation window 15', and the center axle of a treatment instrument channel opening 17' is arranged at a distance t2 (t1<t2) shown in the figure away from the center axle of the observation window 15' of the distal end portion 4'. From the physical relationship between the observation window 15' provided at the second objective optical system 37 of the viewing angle α2 and the treatment instrument channel opening 17' positioned at the distance t2 from the observation window 15', the treatment instrument 51 penetrating and projecting from the treatment instrument channel opening 17' toward the observed region needs to exceed the amount of projection l in the figures to project in order to proceed in the range of the viewing angle α2 of the second objective optical system 37. That is, by projecting the treatment instrument 51 of the second electronic endoscope 32 more than the amount of projection l, the treatment instrument 51 can proceed in the range in the wide viewing angle α2 of the second objective optical system 37.

That is, as the treatment instrument 51 of the second electronic endoscope 32 is operated to project the same amount of projection l as the treatment instrument 51 of the first electronic endoscope 31 as shown in FIG. 1A, the treatment instrument can be recognized in the respective observation image. Accordingly, the operator feels substantially the same when operating to project the respective treatment instrument 51 for the first and the second electronic endoscopes 31, 32, and at the same time the amount of projection of the treatment instrument 51 from the end surface of the distal end portions 4, 4' becomes substantially the same, and thus the physical relationship between the observed region and the treatment instrument 51 is substantially the same.

As described above, the physical relationship between the observation window 15 provided at the distal end portion 4 of the insertion unit 2 and the treatment instrument channel opening 17, while the amount of projection of the treatment instrument 51 projecting from the treatment instrument channel opening 17 being substantially the same, is set according to the viewing angle of the objective optical systems 33, 37 provided in the observation window 15, thereby preventing the operator from feeling uncomfortable as to the operational feeling of the treatment instrument 51 and the physical relationship between the observed region and the treatment instrument.

In addition, as applying the above concept, regarding a single electronic endoscope, it is beneficial that the distance between the objective optical system at the insertion unit end and the treatment instrument channel opening is determined based on the viewing angle of the objective optical system. Concretely, for example, the distance between the objective optical system and the treatment instrument channel opening should be determined in order for the image of the end of the treatment instrument to be displayed in the predetermined reference area on the observation image obtained by the objective optical system when the amount of projection of the treatment instrument projecting from the treatment instrument channel opening reaches the predetermined value.

As described above, the conventional electronic endoscope, which sets the distance between the objective optical system and the treatment instrument channel opening based on such as the diameter of the insertion unit and the size of the objective optical system, when the field of view of the objective optical system is different, can adversely affect the operation of the operator because of the different amount of projection of the treatment instrument even if the treatment instrument is displayed at the identical position in the observation image. For the purpose of resolving the above problem, it is beneficial to realize the electronic endoscope in which the distance between the objective optical system and the treatment instrument channel opening is set so as to display the image of the end of the treatment instrument in the predetermined reference area in the observation image when the treatment instrument projects the predetermined reference value for the predetermined amount of projection of the treatment instrument. The distance to satisfy this condition is determined according to the viewing angle of the objective optical system as described above, and for example in the case of FIG. 1A, the distance between the objective optical system and the treatment instrument channel opening is t1 based on the viewing angle α1 of the objective optical system, and in the case of FIG. 1B, the distance between the objective optical system and the treatment instrument channel opening is t2 based on the viewing angle α2. As such, by employing the electronic endoscope with the determined distance between the objective optical system and the treatment instrument channel opening based on the viewing angle, even if the electronic endoscope of different viewing angle is used, the operator can refer to the observation image to understood how much the treatment instrument is projected easily, thereby significantly improving the operability of the electronic endoscope.

The reference area on the observation image can be arbitrary area; however, it is preferable that the peripheral region of the observation image is set as the reference area as shown in the example of FIG. 1. As such, by setting the reference area, when the treatment instrument is gradually projected, it is an advantage that the operator can easily recognize that the amount of projection of the treatment instrument reaches the predetermined reference value immediately upon displaying the image of the end of the treatment instrument in the observation image.

As an example of the electronic endoscope, which has the determined distance between the objective optical system and the treatment instrument channel opening based on the viewing angle of the objective optical system, it is preferable that the distance between the objective optical system and the treatment instrument channel opening is set so that a part of the treatment instrument projecting from the treatment instrument channel opening, which exists within the field of view of the objective optical system determined based on the viewing angle, is arranged at a position farther from the objective optical system than a near point. A near point means a point at the shortest distance for the operative system to be able to produce the image. By setting the distance between the objective optical system and the treatment instrument channel opening so that the treatment instrument is arranged at a point farther from the objective optical system than the near point within the field of view of the objective optical system, the image of the treatment instrument displayed in the observation image always becomes clear, and the operator can easily recognize that the treatment instrument is displayed in the observation image.

FIGS. 1A and 1B are referred for the explanation of an example of determining the distance. Furthermore, in order to simplify the explanation below, the near points for the first objective optical system 33 and the second objective optical system 37 exist in the area where the distance from the objective optical system is d0 and establishes the relationship of d1>d0>d2 relative to the later described d1, d2.

In FIG. 1A, when the viewing angle of the first objective optical system 33 is α1, the minimum value of the distance d between the part of the treatment instrument 51 existing in the field of view of the first objective optical system 33 and the first objective optical system 33 (precisely, the observation window 15 forming the first objective optical system 33 in FIG. 1A) becomes d1 (>d0), and the treatment instrument 51, within the viewing angle, is positioned farther from the first objective optical system 33 than the near point. Therefore, at the first electronic endoscope 31 equipped with the first objective optical system 33 of the viewing angle α1, the image of the treatment instrument 51 displayed on the observation image is very clear, which eliminates problems such as giving a possibility of the operator to feel uncomfortable.

On the other hand, in FIG. 1A, the viewing angle α2 has the different situation. When the first objective optical system 33 has the viewing angle α2, as shown in FIG. 1A, the minimum value of the distance d between the part of the treatment instrument 51 existing in the field of view of the first objective optical system 33 determined by the viewing angle α2 and the first objective operative system 33 becomes d2, which creates a situation where the distance from the first objective optical system 33 in the field of view becomes smaller than the distance d0 to the near point. Therefore, in the case of the wide viewing angle α2, the image of the treatment instrument 51 in the observation image may become unclear, which gives the problems such as giving the operator uncomfortable feeling.

In consideration of the above two cases of viewing angle α1 and α2, it is necessary for the minimum value of the distance d between the first objective optical system 33 and the treatment instrument 51 to become d0 or above in order to avoid the problems. Furthermore, as shown in FIG. 1A, the minimum value of the distance d can be determined by the distance between the area where the limit of field of view of the first objective optical system 33 and the treatment instrument 51 cross and the first objective optical system 33. Accordingly, when the viewing angle is enlarged, it is preferable to form the treatment instrument channel 26 so that the distance between the cross area and the first objective optical system 33 becomes d0 or above, and more concretely, preferably, the distance between the treatment instrument channel opening 17 and the first objective optical system 33 is determined to be d0 or above. By setting the position of the treatment instrument channel opening 17 satisfying the conditions above, for example as shown in FIG. 1B, similarly for the viewing angle α2, the minimum value of the distance d can be d1 (>d2), thereby displaying the image of the treatment instrument 51 on the observation image clear. In addition, such a structure is preferably employed in the electronic endoscope equipped with the wide angle objective optical system with 150 degrees or more of viewing angle. This is because especially when the field of view is wide angle, the image of the treatment instrument on the observation image tends to become unclear.

Here, if the number of pixels of the first CCD 34 and the second CCD 38 of the first and second electronic endoscopes 31, 32 and the aspect ratio thereof are the same, the range of the observed region image formed in the first and second CCDs 34, 38 varies for each of the first objective optical system 33 of the viewing angle α1 and the second objective optical system 37 having the viewing angle α2 with wider angle than the viewing angle α1 of the first objective optical system 33.

That is, comparing to the area of the observed region displayed in the endoscope image display area 11a on the monitor 11 as being imaged by the first electronic endoscope 31, the area of the observed region displayed in the same endoscope image display area on the monitor 11 as being imaged by the second electronic endoscope 32 is wider. However, individual observed region among observed regions with wide area being displayed on the monitor 11 as being imaged by the second electronic endoscope 32 is smaller comparing to individual observed region among observed regions being displayed on the monitor 11 as being imaged by the first electronic endoscope 31. Furthermore, because the number of pixels of individual observed region among the wide observed regions is small, there is a possibility of displaying unclear image.

Here, high pixel CCD which provides higher number of pixels than the first CCD 34 of the first electronic endoscope 31 is used for the second CCD 38 of the second electronic endoscope 32 having the second objective optical system 37 having the wide viewing angle α2.

By increasing the pixel of the second CCD 38 of the second electronic endoscope 32, based on the second objective optical system 37 having the viewing angle α2, the pixel of the image (observation image 9 of the observed region displayed on the monitor 11 from the image signal is higher than that of the first electronic endoscope 31, thereby improving the resolution of the entire image of the observed region of the second electronic endoscope 32 and the individual observed region among the images of the observed regions. Furthermore, a zoom process is electronically performed on the high pixel image of the observed region generated by the high pixel second CCD 38 of the second electronic endoscope 32, thereby restricting the degradation of the resolution because of its high pixel image even if a zoomed observed region is displayed.

As explained above, the electronic endoscope having the objective optical system with wide viewing angle restricts the degradation of the image quality for the individual observed region within the wide image area and electronically zoomed observed region by using the zoomed high pixel CCD.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system, comprising:
a first endoscope that includes a first distal end portion, a first observation window provided at the first distal end portion, a first objective optical system optically coupled to the first observation window and having a first viewing angle, and a first treatment instrument channel opening adapted to allow a first treatment instrument to be inserted thereinto; and
a second endoscope that includes a second distal end portion, a second observation window provided at the second distal end portion, a second objective optical system optically coupled to the second observation window and having a second viewing angle wider than the first viewing angle, and a second treatment instrument channel opening adapted to allow a second treatment instrument to be inserted thereinto, wherein
a first distance between the first treatment instrument channel opening and the first observation window is shorter than a second distance between the second treatment instrument channel opening and the second observation window, and the first distance is a tangent of one-half of the first viewing angle, multiplied by a predetermined constant, and the second distance is a tangent of one-half of the second viewing angle, multiplied by the predetermined constant so that the first treatment instrument is allowed to be in a range of the first viewing angle and the second treatment instrument is allowed to be in a range of the second viewing angle when an amount of projection of the first treatment instrument from the first treatment instrument channel opening is longer than a predetermined value and an amount of projection of the second treatment instrument from the second treatment instrument channel opening is longer than the predetermined value.

2. The endoscope system according to claim 1, wherein
the first endoscope includes a first solid imaging element at an image formation position of the first objective optical system, and
the second endoscope includes a second solid imaging element at an image formation position of the second objective optical system, the second solid imaging element having a number of pixels larger than that of the first solid imaging element.

3. The endoscope system according to claim 1, wherein
an image of an end of the first treatment instrument is allowed to appear in a first reference area in a first observation image of an area determined by the first viewing angle when an amount of projection of the first treatment instrument from the first treatment instrument channel opening reaches a reference value; and
an image of an end of the second treatment instrument is allowed to appear in a second reference area in a second observation image of an area determined by the second viewing angle when an amount of projection of the second treatment instrument from the second treatment instrument channel opening reaches the reference value.

4. The endoscope system according to claim 3, wherein
the first reference area is a peripheral region of the first observation image; and
the second reference area is a peripheral region of the second observation image.

5. The endoscope system according to claim 1, wherein
the second viewing angle of the second objective optical system is 150 degrees or more;
a part of the first treatment instrument in a space area of a field of view of the first objective optical system determined by the first viewing angle allowed to be farther than a near point of the first objective optical system, with the first treatment instrument inserted into the first treatment instrument channel opening; and
a part of the second treatment instrument in a space area of a field of view of the second objective optical system determined by the second viewing angle is allowed to be farther than a near point of the second objective optical system, with the second treatment instrument inserted into the second treatment instrument channel opening.

* * * * *